(12) United States Patent
Biwa

(10) Patent No.: US 7,487,061 B2
(45) Date of Patent: Feb. 3, 2009

(54) SAMPLE ANALYZER

(75) Inventor: Seido Biwa, Kobe (JP)

(73) Assignee: Sysmex Corporation, Kobe (JP)

( * ) Notice: Subject to any disclaimer, the term of this patent is extended or adjusted under 35 U.S.C. 154(b) by 474 days.

(21) Appl. No.: 10/442,288

(22) Filed: May 20, 2003

(65) Prior Publication Data

US 2003/0220761 A1    Nov. 27, 2003

(30) Foreign Application Priority Data

May 23, 2002    (JP)    ............................. 2002-149583

(51) Int. Cl.
*G01D 1/00*    (2006.01)
(52) U.S. Cl. .................................... 702/127
(58) Field of Classification Search ................ 702/127; 435/6, 69.1, 69; 514/12; 235/386; 436/70, 436/514; 422/64, 102, 49, 63, 65; 604/409; 600/575, 576; 250/458; 346/33; 524/556
See application file for complete search history.

(56) References Cited

U.S. PATENT DOCUMENTS 4,820,297 A * 4/1989 Kaufman et al. ............ 604/409
5,150,795 A    9/1992 Nakayama et al.
5,209,903 A    5/1993 Kanamori et al.
5,524,496 A    6/1996 Nagai et al.
5,737,078 A    4/1998 Takarada et al.
6,162,399 A * 12/2000 Martinell Gisper-Sauch . 422/64
6,255,614 B1    7/2001 Yamakawa et al.
2002/0034824 A1    3/2002 Abo
2002/0168657 A1 * 11/2002 Chen et al.
2004/0005245 A1 * 1/2004 Watson et al. ................ 422/65

FOREIGN PATENT DOCUMENTS

| EP | 0700719 A1 | 3/1996 |
| JP | 64-20450 | 1/1989 |
| JP | 08-075753 | 3/1996 |
| JP | 08-304410 | 11/1996 |
| JP | 2002-040033 | 2/2002 |

* cited by examiner

*Primary Examiner*—Tung S Lau
(74) *Attorney, Agent, or Firm*—Brinks Hofer Gilson & Lione

(57) ABSTRACT

A sample analyzer includes a marking unit containing a marker for marking a container containing a sample, and a controller for controlling the marking unit based on sample information. A sample analyzing method includes a) providing a container containing a sample, b) obtaining the sample from the container, c) detecting a signal from the obtained sample, d) analyzing the detected signal, e) determining whether marking the container is needed or not based on sample information; and f) automatically marking the container if marking is needed.

23 Claims, 13 Drawing Sheets

Fig5

| analysis item | range of normal value | |
|---|---|---|
| | lower limit value | upper limit value |
| WBC | 3200 | 9300 |
| RBC | 350 | 580 |
| Hgb | 11.5 | 18.5 |
| PLT | 10 | 35 |

| ID | necessary to recheck |
|---|---|
| 0001 | need |
| 0002 | not need |
| 0003 | not need |
| 0004 | need |
| 0005 | not need |
| 0006 | not need |
| 0007 | not need |
| 0008 | not need |
| 0009 | not need |
| 0010 | not need |
| 0011 | need |
| | |
| | |
| | |

| ID | risk information |
|---|---|
| 0001 | high |
| 0002 | low |
| 0003 | low |
| 0004 | low |
| 0005 | high |
| 0006 | low |
| 0007 | high |
| 0008 | low |
| 0009 | low |
| 0010 | low |
| 0011 | high |
| 0012 | low |
| 0013 | low |
| 0014 | low |
| 0015 | high |
| 0016 | low |
| 0017 | high |
| 0018 | low |
| 0019 | high |
| 0020 | low |
| | |
| | |
| | |

150

SAMPLE ANALYZER

BACKGROUND

The present invention relates to sample analyzers, for example, blood analyzers, biochemical analyzers, urine analyzers, industrial particle analyzers, and the like.

Sample analyzers such as conventional blood analyzers incorporate a body for analyzing samples, and a conveyor for conveying a rack. A row of sample containers containing sample material are arrayed on the rack. A bar code representing an identification number (ID) is affixed to the sample container to identify the sample material. The conveyor is provided with a rack conveying mechanism and a stock unit (rack recovery part) The rack conveying mechanism accommodates the rack, and conveys the rack to the stock unit (rack recovery part). The body is provided with a bar code reader, suction unit, and analysis unit. The body reads the ID of the sample container conveyed by the rack conveying mechanism, suctions the sample material from within the sample container, and analyzes the suctioned sample material.

Analyzed samples may need re-examination when analysis results are anomalous, and particular care must be exercised in handling because the sample materials housed in the internal units may be infected with an infectious virus. Accordingly, the users of the sample analyzer must recognize whether re-examination of the sample is needed and the sample is infected with an infectious virus.

In conventional sample analyzers, however, a user must read the ID from a sample container accommodated in the rack recovery unit, and compare the ID, analysis result, and virus infection status in order to recognize whether re-examination is needed and the sample is infected. This operation is extremely complex.

A conventional specimen sorting apparatus has a path of conveyance including a rack transporting conveyor and a rack sorting conveyor connected to the downstream end of the rack conveyor, a rack supply conveyor provided at one side of the rack transporting conveyor, a first specimen bar code reader disposed in the vicinity of the rack supply conveyor, a printer disposed near the downstream end of the rack transporting conveyor and adapted to operate in accordance with instructions given by a host computer, a rack bar code reader and a second specimen bar code reader disposed along the path of conveyance between the rack supply conveyor and the printer, a table disposed at one side of the rack sorting conveyor and having a predetermined number of storage sections defined thereon and a plurality of pusher mechanisms arranged along the rack sorting conveyor and associated with the respective storage sections (see U.S. Pat. No. 5,150,795).

A conventional specimen-container transfer apparatus has a conveyance unit for transferring specimen-container racks, a specimen-container ID reader for reading specimen-container identification signals from the specimen-container racks transported by the conveyance unit; a specimen-container housing rack table on which specimen container housing racks for housing specimen containers can be set up; specimen-container transfer means for taking specimen containers out of specimen-container racks and putting them into specimen-container housing racks; and a control unit for controlling the order in which the specimen containers are put into the specimen-container housing rack (see U.S. Pat. No. 6,255,614).

For example, although specimens needing re-examination and samples not needing re-examination can be sorted in the above mentioned specimen sorting apparatus and specimen-container transfer apparatus, these apparatuses are disadvantageously large and complex.

SUMMARY

The scope of the present invention is defined solely by the appended claims, and is not affected to any degree by the statements within this summary.

By way of introduction, an object of the present invention is to provide a sample analyzer provided with a marking mechanism for marking a specific sample container.

In a first aspect, the invention provides a sample analyzer including: a marking. unit containing a marker for marking a container containing a sample, and a controller for controlling the marking unit based on sample information.

In a second aspect, the invention provides a sample analyzer including: a detector for detecting a signal from a sample, a marking unit for marking a container containing the sample, and a controller for analyzing the signal detected by the detector, determining whether the sample is to be rechecked or not based on the result of analyzing the signal, and driving the marking unit to mark the container if the sample is. to be rechecked.

In a third aspect, the invention provides a sample analyzing method that includes: a) providing a container containing a sample, b) obtaining the sample from the container, c) detecting a signal from the obtained sample, d) analyzing the detected signal, e) determining whether marking the container is needed or not based on the sample information, and f) automatically marking the container if marking is needed.

BRIEF DESCRIPTION OF THE DRAWINGS

FIG. 5 is an illustration of the normal value table 146;

FIG. 6 is an illustration of the recheck table 148;

FIG. 10 is an illustration of a controller 201a;

FIG. 11 is an illustration of the contents of the risk table 150;

FIG. 13 is an illustration of the structure of the marking mechanism 215a.

DETAILED DESCRIPTION OF THE PRESENTLY PREFERRED EMBODIMENTS

The present invention is described hereinafter based on the representative embodiments shown in the accompanying drawings. The sample analyzer of the present invention is described using a blood analyzer as an illustrative and non-limiting example. This description should not be considered to limit the invention in any way.

Figure 1:
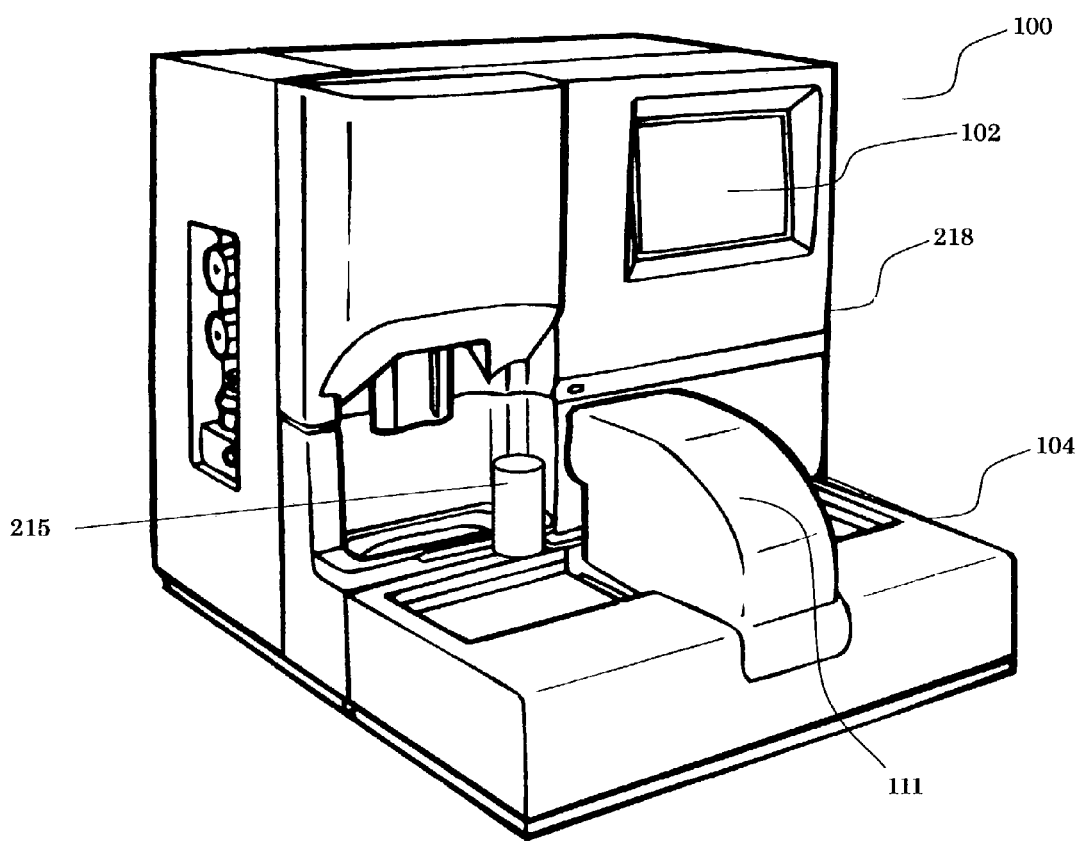
FIG. 1 is a perspective view of a blood analyzer of an embodiment of the present invention.

FIG. 1 is a perspective view of the blood analyzer of a first embodiment of the present invention. The blood analyzer 100 comprises a body 218 and a conveyor 104. The body 218 is provided with a touch panel display 102 or the like. The conveyor 104 is provided with a mixing-suctioning mechanism 111, marking mechanism 215 or the like.

The body 218 has the function of calculating the number and distribution of corpuscles in the blood, and, for example, the body of model SF-3000 (Sysmex Corp.) may be used in this hardware structure.

Furthermore, for example, the conveyor of model SF-3000 (Sysmex Corp.) may be used in the hardware structure of the conveyor 104 excluding the marking mechanism 215.

Figure 2:
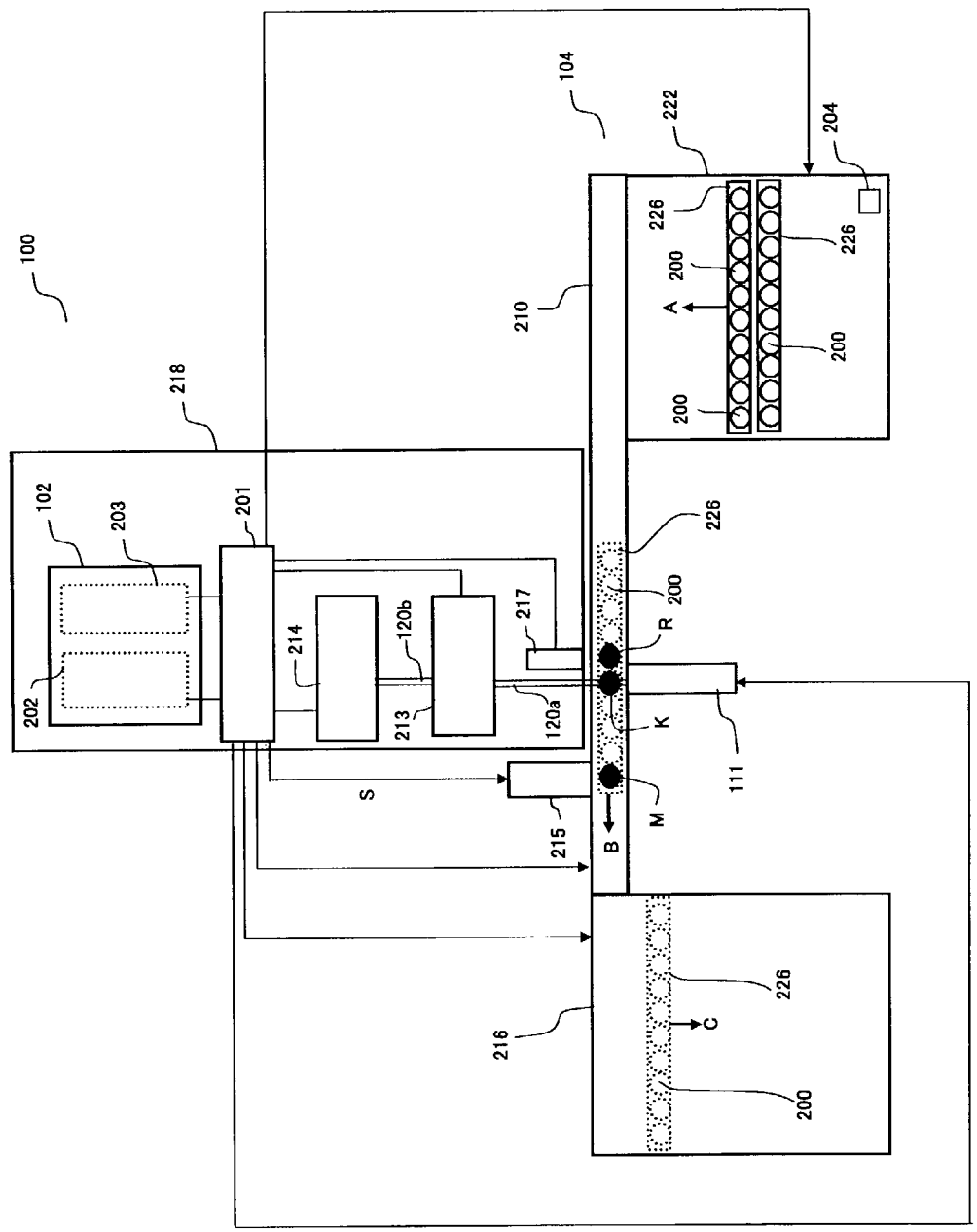
FIG. 2 is an illustration of the blood analyzer 100.

FIG. 2 is an illustration of the structure of the blood analyzer 100.

First, the conveyor 104 is described below.

The conveyor 104 is provided with a rack conveyance mechanism 222, rack transverse feeding mechanism 210, rack recovery mechanism 216, mixing-suctioning mechanism 111, and marking mechanism 215.

The rack conveyance mechanism 222 holds a rack 226 accommodating a plurality of sample containers 200, and transports the rack 226 in the arrow direction A. The rack conveyance mechanism 222 is provided with a start switch 204 for starting the transport of the rack 226.

Figure 3:
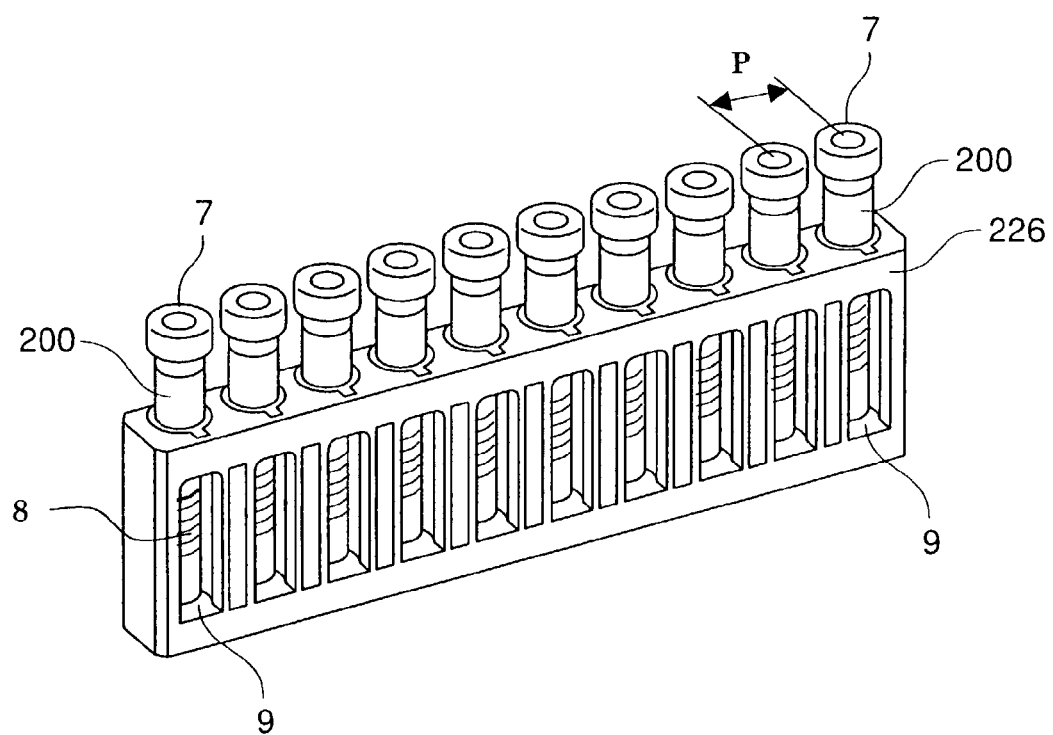
FIG. 3 is a perspective view of the rack 226 and sample container 200.

As shown in FIG. 3, the rack 226 has a test tube rack configuration, and is capable of accommodating 10 sample containers 200. The rack 226 is provided with a slit 9 in a vertical direction to allow reading of a bar code 8 affixed to the sample container 200. The sample container 200 is a container having a closed bottom and cylindrical shape essentially like a test tube, containing blood, and with the opening at the top end blocked with a rubber cap 7. The bar code 8 represents an ID for discriminating the blood contained within the sample container 200. In addition to the ID, the bar code 8 may also include information representing the sample collection conditions and information identifying the patient from whom the blood was collected. Alternatively, an IC chip may be used instead of the bar code 8. The reference symbol P represents the distance between adjacent sample containers, and this distance is designated 1 pitch.

Returning to FIG. 2, the conveyor 104 is described below.

The rack transverse feeding mechanism 210 transports the rack 226, being conveyed by the rack conveyance mechanism 222, in the arrow direction B (transverse feed). The rack transverse feeding mechanism 210 transverse feeds the rack 226 in 1-pitch increments. Accordingly, it is possible to determine at which position of the rack transverse feed mechanism 210 a sample container 200 being checked is at by the number of transverse feeds of the rack 226 performed by the rack transverse feeding mechanism 210.

The reference symbol R represents the bar code reading position. The bar code reading position R is opposite the bar code reader 217 fixedly attached to the body 218. If a sample container 200 is present at the bar code reading position R, the bar code reader 217 can read the bar code 8 (refer to FIG. 3) affixed to the sample container 200 through the slit 9 (refer to FIG. 3).

Reference symbol K represents the container retrieval position. The container retrieval position K is opposite the mixing-suctioning mechanism 111 fixedly attached to the transverse feeding mechanism 210. If a sample container 200 is present at the container retrieval position K, the mixing-suctioning mechanism 111 can remove the sample container 200 from the rack 226.

Reference symbol M represents the marking position. This position is opposite the marking mechanism 215 fixedly attached to the transverse feeding mechanism 210. If a sample container 200 is present at the marking position M, the marking mechanism 215 can mark (i.e., apply a mark to) the sample container 200.

The distance between the bar code reader position R and the container retrieval position K is 1 pitch, and the distance between the bar code reader position R and the marking position M is 5 pitches.

The rack recovery mechanism 216 transports the rack 226, which is being transported by the rack transverse feeding mechanism 210, in the arrow direction C for recovery.

The mixing-suctioning mechanism 111 is disposed between the rack conveyance mechanism 222 and the rack recovery mechanism 216. The mixing-suctioning mechanism 111 removes a sample container 200 disposed at the container retrieval position K from the rack 226 transversely fed by the rack transverse feeding mechanism 210, mixes the contents of the sample container 200, suctions only a predetermined amount of the sample from the container, and thereafter returns the sample container 200 to its original location in the rack 226. The mixing-suctioning mechanism 111 also may be fixedly attached to the body 218 next to the transverse feeding mechanism 210.

The marking mechanism 215 is fixedly attached to the transverse feeding mechanism 210. The marking mechanism 215 is fixedly attached at a position which allows the marking of a sample container 200 after the bar code reader 217 has read the bar code and the sample has been suctioned by the mixing-suctioning mechanism 111. The marking mechanism 215 also may be fixedly attached to the body 218 adjacent to the transverse feeding mechanism 210. The structure of the marking mechanism 215 is described layer.

The body 218 is described below.

The body 218 is provided with a touch panel display 102, controller 201, sample regulating mechanism 213, detecting mechanism 214, and bar code reader 217.

The sample regulating mechanism 213 is connected to the mixing-suctioning mechanism 111 by a tube 120a, and performs processing such as measurement, dilution, hemolysis and the like of the suctioned sample, and transports the sample to the detection mechanism 214 through a tube 120b. A sampling valve, for example, such as that disclosed in U.S. Pat. No. 5,524,496 may be used as the sample regulating mechanism 213. The tube 120a is arranged in the interior part of the transverse feeding mechanism 210, so as not to hinder the operation of the rack 226.

The detecting mechanism 214 digitizes an optical signal obtained from the optical irradiation of a sample transported from the sample regulating mechanism 213 and an electrical signal obtained from current flowing through a sample transported from the sample regulating mechanism 213, and transmits the digitized signals to the controller 201. A flow cytometer, for example, such as that described in U.S. Pat. No. 5,737,078, and an electrical resistance-type sensor unit, for example, such as that described in United States Patent Publication No. 2002-0034824 may be used as the detecting mechanism 214.

The touch panel display 102 combines an input unit 202 and an output unit 203.

The input unit 202 receives information input from a user, and transmits it to the controller 201.

The output unit 203 displays information transmitted from the controller 201.

The bar code reader 217 reads the identification information (ID) from the bar code 8 (refer to FIG. 3) affixed to the sample container 200, and the read ID is transmitted to the controller 201. Alternatively, when an IC chip is used instead of a bar code, an IC chip reader is used instead of the bar code reader 217.

The controller 201 is a microcomputer including a central processing unit (CPU), read only memory (ROM), random access memory (RAM), hard disk drive (HDD) and the like. A signal S, which is transmitted in the arrow direction from the controller 201 to the marking mechanism 215, represents a signal output from the controller 201 to the marking mechanism 215.

Figure 4:
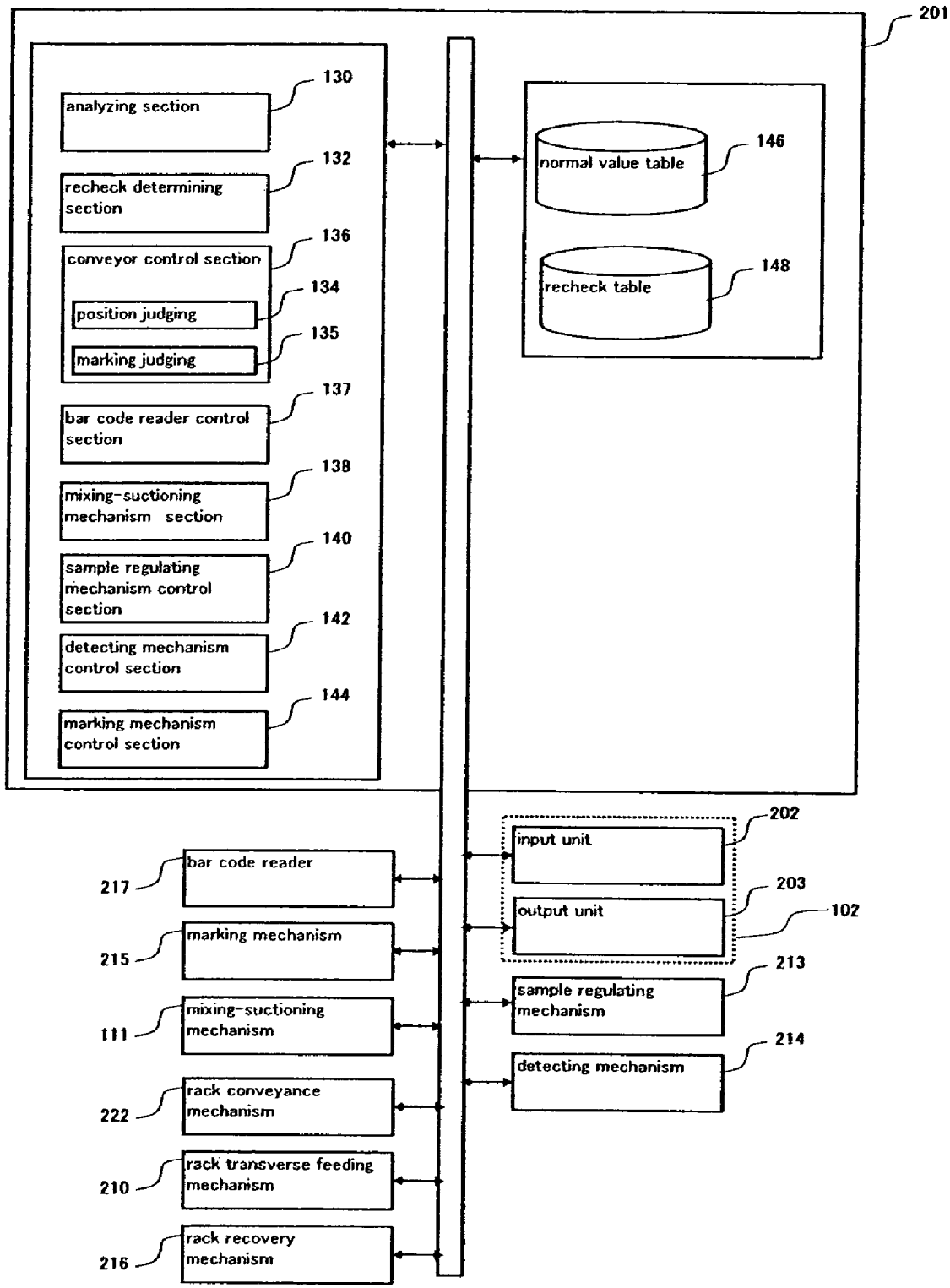
FIG. 4 is an illustration of the controller 201.

The internal structure of the controller 201 is explained below with reference to FIG. 4.

The controller 201 is provided with an analyzing section 130, recheck determining section 132, conveyor control section 136, bar code reader control section 137, mixing-suctioning mechanism 138, sample regulating mechanism control section 140, detecting mechanism control section 142, marking mechanism control section 144, normal value table 146, and recheck table 148. The conveyor control section 136 is provided with a position judging section 134 and a marking judging section 135. Connected to the controller 201 are the rack conveyance mechanism 222, rack transverse feeding mechanism 210, rack recovery mechanism 216, mixing-suctioning mechanism 111, input unit 202, output unit 203, sample regulating mechanism 213, detecting mechanism 214, marking mechanism 215, and bar code reader 217.

The analyzing section 130 calculates the analysis results (number of leukocytes, number of erythrocytes, number of platelets, hemoglobin concentration and the like) from the optical signals and electrical signals transmitted from the detecting mechanism 214, and associates the calculated analysis results together with the ID read by the bar code reader 217 and temporarily stores them.

The recheck determining section 132 determines whether or not it is necessary to recheck the sample from the analysis results temporarily stored in the analyzing section 130 using the normal value table 146, and stores this result together with the ID in the recheck table 148.

FIG. 5 is an illustration of the contents of the normal value table 148. The normal value table 148 stores the range of normal values (lower limit value and upper limit value) associated with the number of leukocytes, number of erythrocytes, number of platelets, and hemoglobin concentration. When the number of leukocytes, number of erythrocytes, number of platelets, and hemoglobin concentration in the analysis results are all within the normal range, the recheck determining section 132 (FIG. 4) determines a recheck is not needed, and determines that a recheck is needed when even one value is outside the normal range. If the optimum and average values are stored beforehand as the range of normal values in the normal value table 146, the recheck determining section 132 also may determine a recheck is needed when the difference between the analysis result and these values is greater than a predetermined value.

FIG. 6 illustrates the content of the recheck table 148. The recheck table 148 associates and stores the ID together with whether there is a need for a recheck as determined by the recheck determining section 132. This example shows samples with IDs 0001, 0004, and 0011 as needing a recheck.

Returning to FIG. 4, the explanation of the content structure of the controller 201 continues below.

The conveyor control section 136 controls the operation of the rack conveyance mechanism 222, rack transverse feeding mechanism 210, and rack recovery mechanism 216.

The position judging section 134 determines the position of the target sample container 200 on the rack transverse feeding mechanism 210. The position of the sample container 200 is determined from the number of times the rack transverse feeding mechanism 210 is operated. When the conveyor control section 136 outputs an instruction for a single operation to the rack transverse feeding mechanism 210, the rack transverse feeding mechanism 210 moves the rack 226 only 1 pitch. As previously mentioned, the distance between the bar code reading position R and the marking position M is 5 pitches (refer to FIG. 2). Accordingly, after the bar code has been read by the bar code reader 217, and after the conveyor control section 136 has output operation instructions 5 times to the rack transverse feeding mechanism 210, the position judging section 134 determines that the sample container 200 whose bar code has been read is at the marking position M. The position judging section 134 may also be constructed by providing a sensor on the rack transverse feeding mechanism 210 so as to judge the position of the sample container 200 based on a signal from this sensor.

The marking judging section 135 determines whether or not marking is needed using the recheck table 148. Specifically, marking is determined to be needed when a sample is judged to need rechecking, and marking is determined to be not needed when a sample is judged to not need rechecking. In this example, since rechecking is needed for samples whose IDs are 0001, 0004, and 0011 (refer to FIG. 6), these samples are judged to need marking, and other samples are judged to not need marking.

The bar code reader control section 137 controls the operation of the bar code reader 217. The mixing-suctioning mechanism control section 138 controls the operation of the mixing-suctioning mechanism 111. The sample regulating mechanism control section 140 controls the operation of the sample regulating mechanism 213. The detecting mechanism control section 142 controls the operation of the detecting mechanism 214. The marking mechanism control section 144 controls the operation of the marking mechanism 215.

A personal computer may also be used for the controller 201 and touch screen display 102.

The controller 201 may be constructed with both a personal computer used as a first control unit provided with an analyzing section 130, recheck determining section 132, normal value table 146, and recheck table 148, and a microcomputer used as a second control unit provided with a conveyor control section 136, bar code reader control section 137, mixing-suctioning mechanism control section 138, sample regulating mechanism control section 140, detecting mechanism control section 142, and marking mechanism control section 144.

Figure 7:
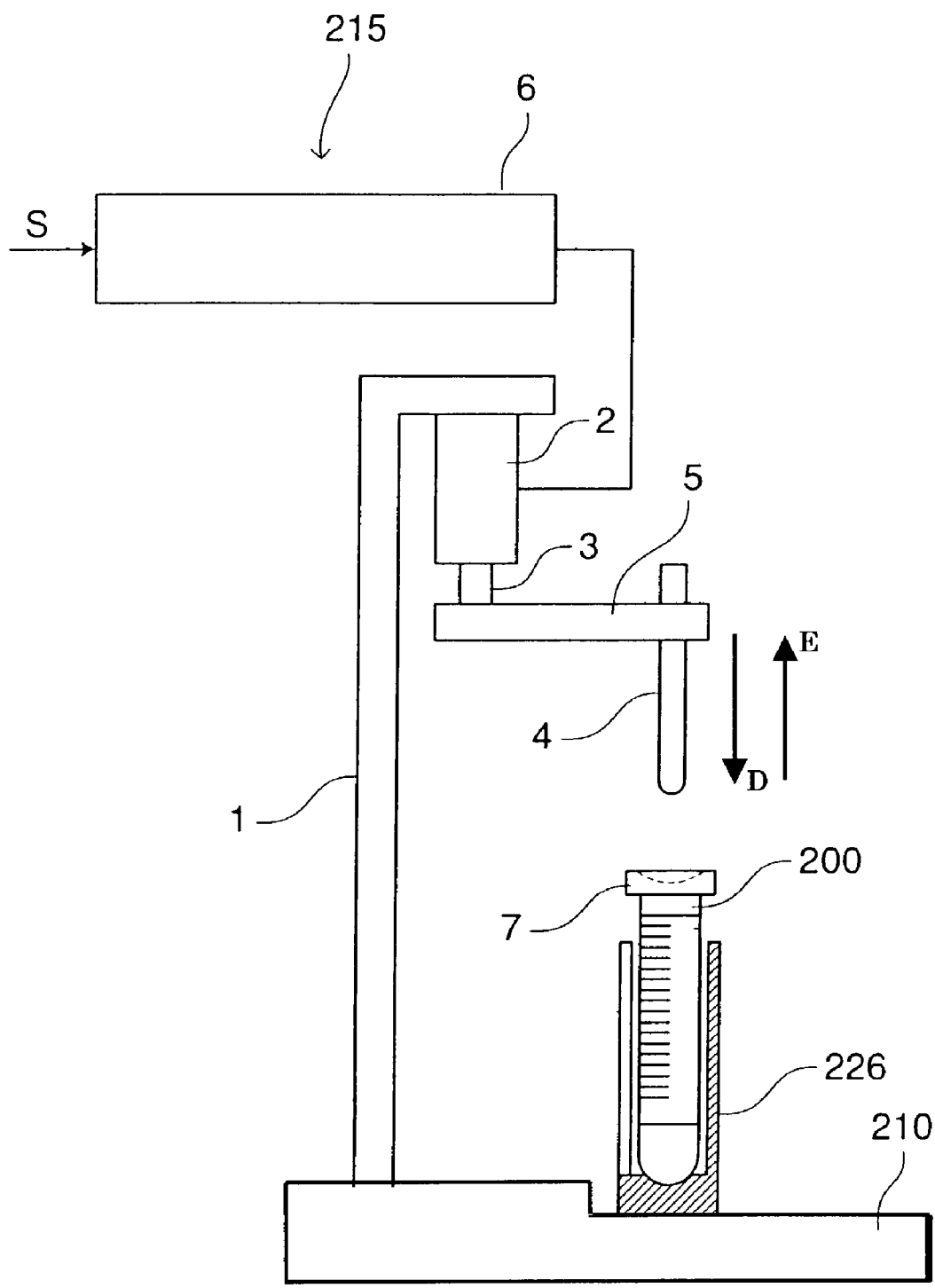
FIG. 7 is an illustration of the marking mechanism 215.

The marking mechanism 215 is described below referring to FIG. 7. FIG. 7 illustrates the structure of the marking mechanism 215. As shown in the drawing, an electric linear actuator 2 is provided on a frame 1 fixedly attached to the transverse feeding mechanism 210, and the drive rod 3 of this linear actuator 2 is connected to a marking pen 4 via an arm 5. By way of example, a metron marker (Asahi Bussan K.K.) can be used as the marking pen 4. Alternatively, instead of the marking pen 4, a marker may be used which has a mechanism to eject ink from a stamp or nozzle, or is constructed so as to affix a seal.

A drive controller 6 provides a driver circuit of the linear actuator 2, so as to receive an output signal S from the marking mechanism control section 144 (see FIG. 4), and drive the linear actuator 2. The marking pen 4 is moved in vertical directions (arrow direction D and arrow direction E) via the drive of the linear actuator 2.

When lowering the marking pen 4, the linear actuator 2 lowers the marking pen 4 to a position at which the tip of the marking pen 4 contacts the cap 7 connected to the top of the sample container 200, and applies ink (marking) on the top surface of the cap 7. Thereafter, the marking pen 4 is returned to the starting position. In this specification, the cap 7 is defined as a part of the sample container 200.

The operation of the blood analyzer 100 is described below with reference to FIGS. 2, 4, 8, and 9.

Figure 8:
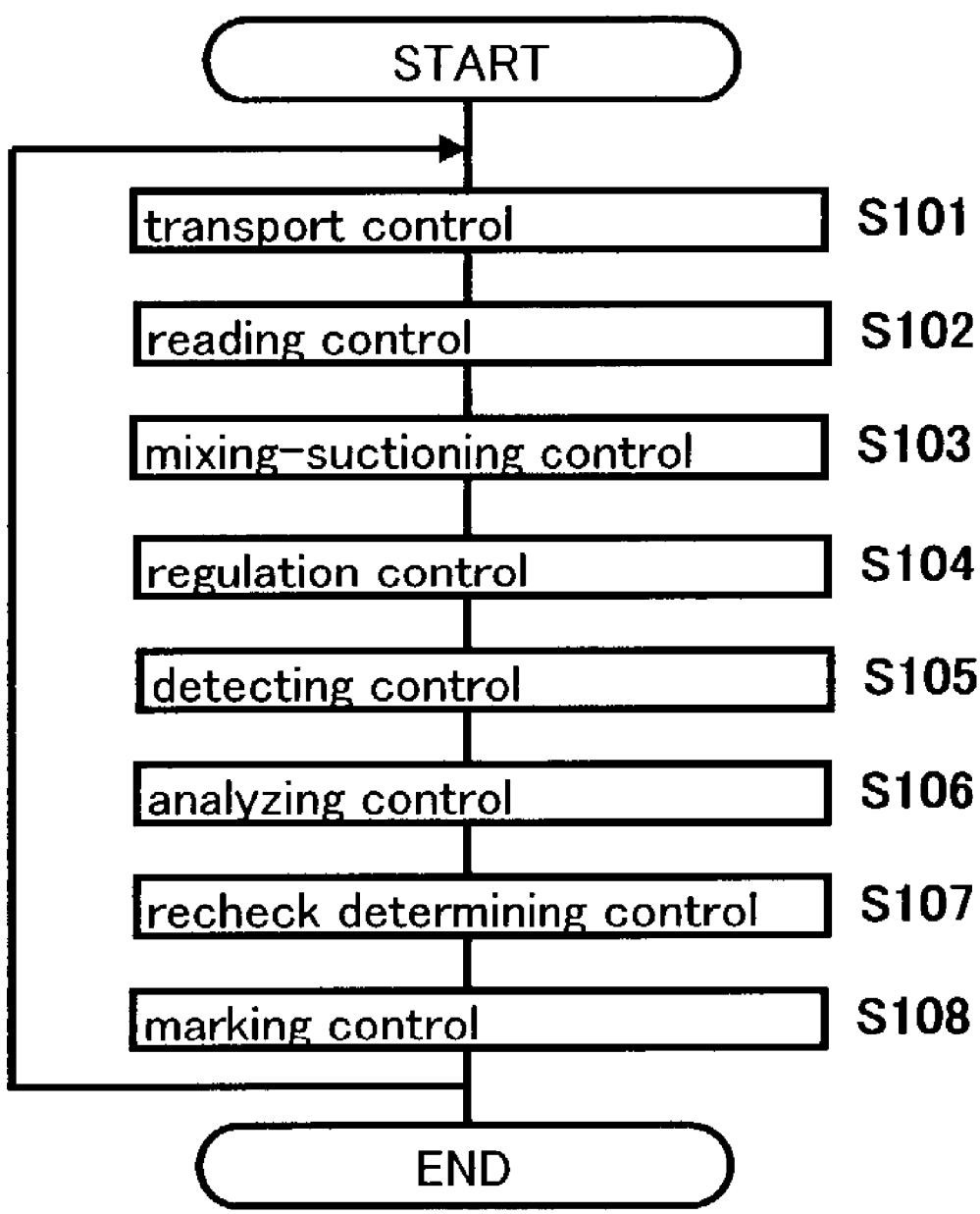
FIG. 8 is a flow chart briefly showing the general processing sequence in the controller 201.

FIG. 8 is a flow chart briefly showing the general processing sequence in the controller 201.

In S101, a process is executed for the conveyor control section 136 to control the transport operation of the rack 226.

In S102, a process is executed for the bar code reader control section 137 to control the reading of a bar code.

In S103, a process is executed for the mixing-suctioning mechanism control section 138 to control the mixing-suctioning operation.

In S104 a process is executed for the sample regulating mechanism control section 140 to control the sample regulating operation.

In S105, a process is executed for the detecting mechanism control section 142 to control the detection operation.

In S106, a process is executed for the analyzing section 130 to control the analysis.

In S107, a process is executed for the recheck determining section 132 to control the determination of the need for a recheck.

In S108, as process is executed for the marking mechanism to control the marking operation.

The processes in S101 through S108 are sequentially repeated.

Figure 9:
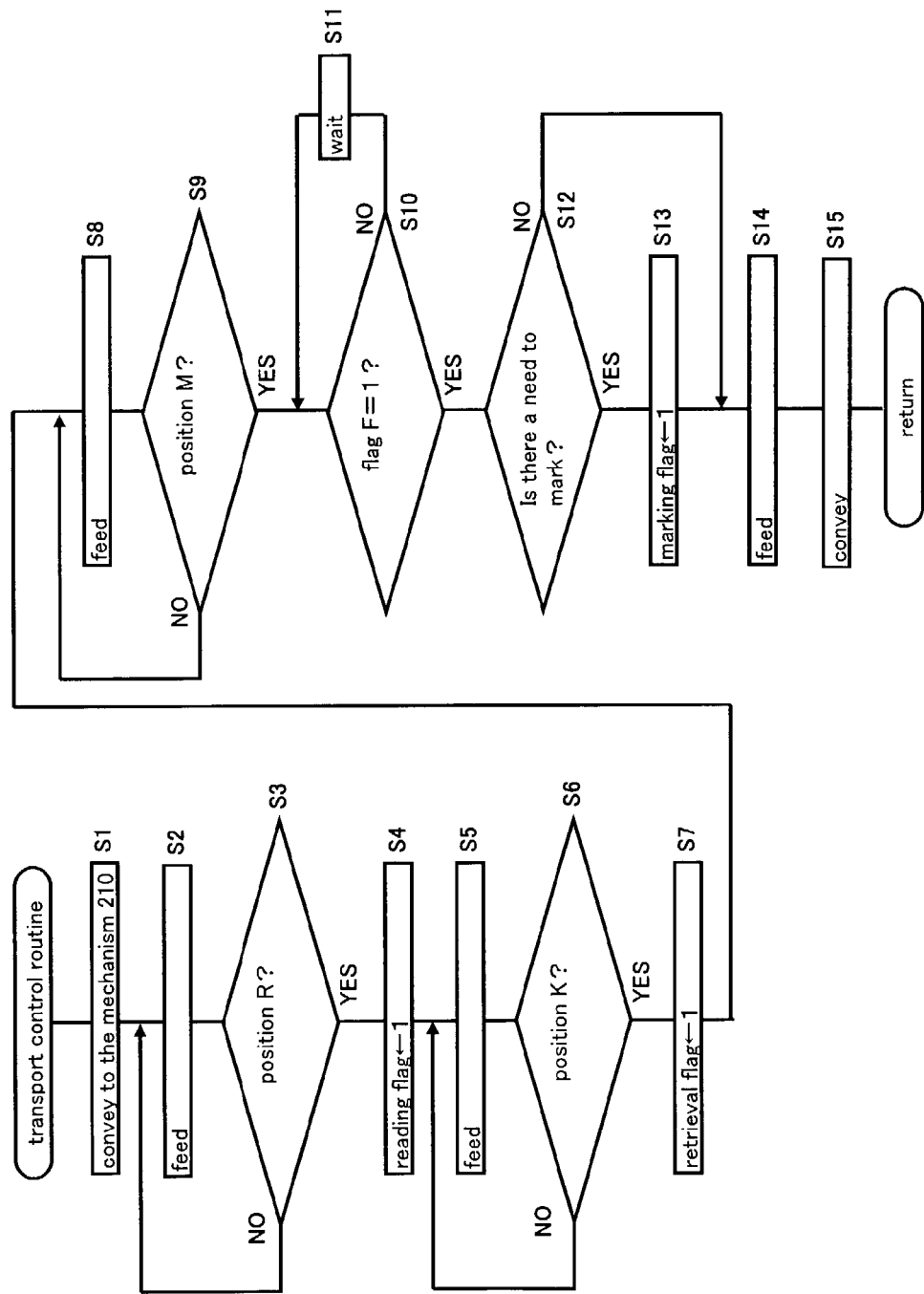
FIG. 9 is a flow chart showing details of the process executed in S101.

FIG. 9 is a flow chart showing details of the process executed in S101.

In S1, a process is executed to convey the rack 226 from the rack conveyance mechanism 222 to the rack transverse feeding mechanism 210.

In S2, a process is executed to transverse feed the rack 226 on the rack transverse feeding mechanism 210 1 pitch.

In S3, a process for judging whether a target sample container 200 is at the bar code reading position R is executed by the position judging section 135. If the sample container 200 is at the bar code reading position R, a process is executed to set a bar code reading flag at [1] (step S4). If the sample container 200 is not at the bar code reading position R, the process of S2 is executed again. In S102 (see FIG. 8), if the bar code reading flag is set at [1], a process is executed to have the bar code reader 217 perform a bar code reading operation.

In S5, after the bar code reading operation by the bar code reader 217 ends, a process is executed to transverse feed the rack 226 on the rack transverse feeding mechanism 210 1 pitch.

In S6, the position judging section 135 executes a process to judge whether the target sample container 200 is at the container retrieval position K. If the sample container 200 is at the container retrieval position K, a process is executed to set a container retrieval flag at [1] (S7). If the sample container 200 is not at the container retrieval position K, the process of S5 is executed again. In S103 (see FIG. 8), if the container retrieval flag is set at [1], a process is executed to have the mixing-suctioning mechanism 111 perform a mixing-suctioning operation. According to this process, the mixing-suctioning mechanism 111 removes the sample container 200 disposed at the container retrieval position K from the rack 226, mixes the container contents, suctions only a predetermined amount of the sample material within the container, and thereafter returns the sample container 200 to its original location in the rack 226.

In S8, after the sample container 200 has been returned to its original location in the rack 226, a process is executed to transverse feed the rack 226 on the rack transverse feeding mechanism 1 pitch.

In S9, the position judging section 135 executes a process for judging whether a target sample container 200 is at the marking position M. If the sample container 200 is at the marking position M, a process is executed to judge whether a [1] has been input to a recheck determining flag F, representing a determination of a need for a recheck (step S10). The input of the recheck determining flag F is executed by the recheck determining section 132 after a need for a recheck has been determined in step S107 (see FIG. 8). However, if the sample container 200 is not at the marking position M, the process of S8 is executed. In S10, if [1] has not been input to the recheck determining flag F, a predetermined wait time elapses (S11), and the process of S10 is executed again.

In S12, the marking judging section 135 executes a process for judging whether there is a need to mark a target sample container 200.

If a need for marking is judged, a process is executed for inputting [1] to a marking flag (S13). However, if marking is judged to be not needed, the process of S13 is not executed. In S108 (see FIG. 8), if the marking flag is set at [1], a process is executed to have the marking mechanism 215 perform a marking operation.

In S14, after the marking of all sample containers needing marking accommodated in the rack 226 has been completed, a process is executed to transverse feed the rack 226 on the rack transverse feeding mechanism 210 to the rack recovery mechanism 216.

In S15, a process is executed to convey the rack 226 on the rack recovery mechanism 216 in the arrow direction C.

According to the blood analyzer having this structure, only the samples needing a recheck are marked. Accordingly, a user may easily and rapidly judge whether to remove a sample container from the rack to perform a recheck, and checking can be quickly and reliably accomplished.

A second embodiment of the sample analyzer of the present invention is described below with reference to the drawings. The sample analyzer of the second embodiment is a blood analyzer in which the internal structure of the controller 201 (FIG. 4) of the previously described blood analyzer 100 has been modified. Accordingly, description of structures other than that of the controller 201 are omitted since these other structures are identical to those of the blood analyzer 100.

Figure 10:
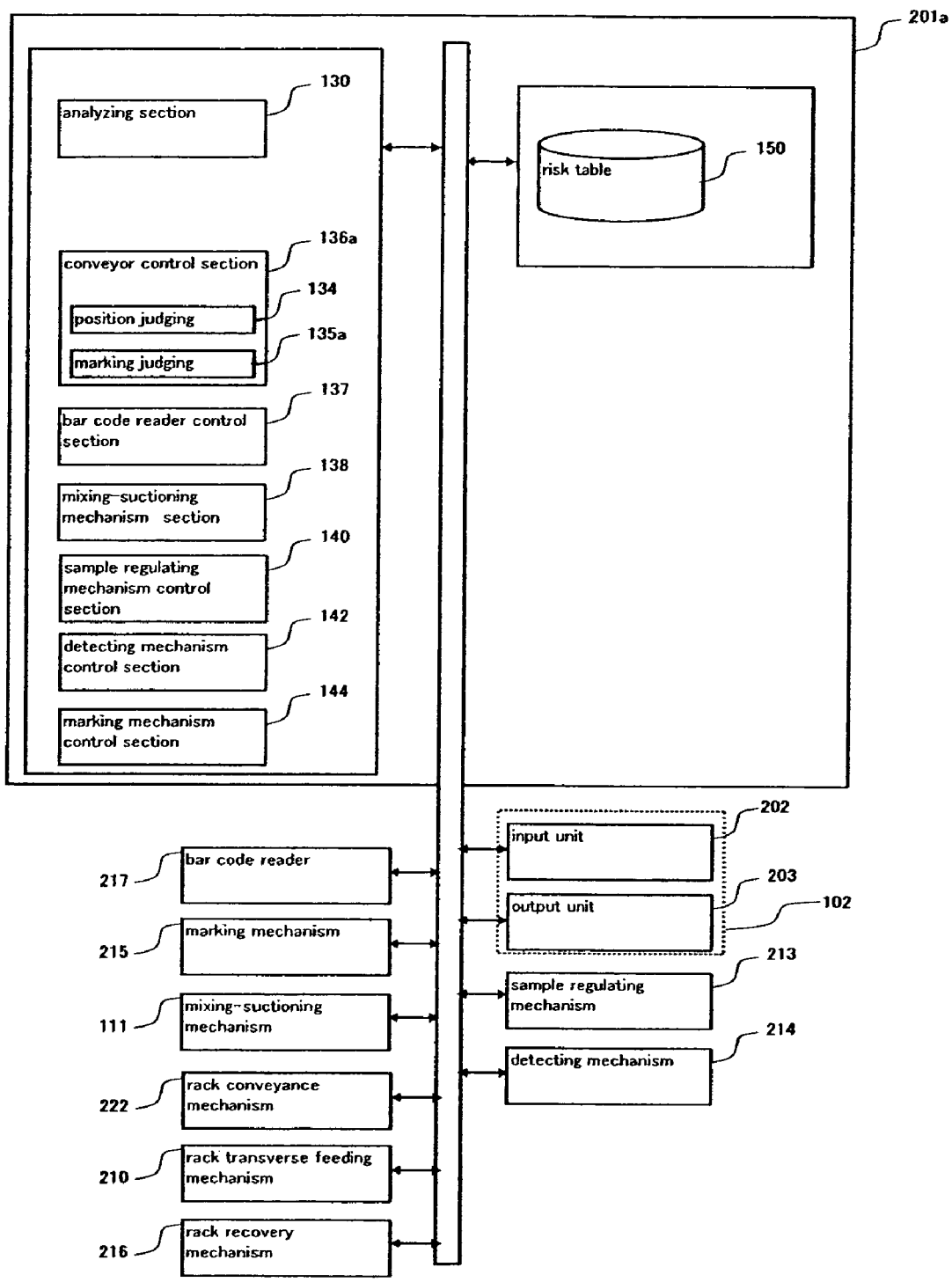

FIG. 10 is an illustration of a controller 201a of a blood analyzer of the second embodiment. The controller 201a is provided with an analyzing section 130, conveyor control section 136a, bar code reader control section 137, mixing-suctioning mechanism control section 138, sample regulating mechanism control section 140, detecting mechanism control section 142, marking mechanism control section 144, and risk table 150. The conveyor control section 136a is provided with a position judging section 134, and a marking judging section 135a. The controller 201a is connected to the rack conveyance mechanism 222, rack transverse feeding mechanism 210, rack recovery mechanism 216, mixing-suctioning mechanism 111, input unit 202, output unit 203, sample regulating mechanism 213, detecting mechanism 214, marking mechanism 215, and bar code reader 217.

FIG. 11 illustrates the content of the risk table 150.

The ID and associated risk information are stored beforehand in the risk table 150. When the patient from whom the target blood sample was collected is infected with an infectious virus such as hepatitis C virus, or the AIDS virus, the user of the blood analyzer must exercise particular care to prevent infection when handling the blood of other patients. Accordingly, risk information of blood collected from patients infected with an infectious virus is set [high], and risk information of blood from other patients is set [low]. This example shows [high] risk information for samples having IDs 0001, 0005, 0007, 0011, 0015, 0017, and 0019.

When a target sample container 200 is set at the marking position M (see FIG. 2), a process is executed to have the marking judging section 135a read the risk information from the risk table 150 associated with the ID (this ID is read by the bar code reader 217) represented by the bar code affixed to the sample container 200, and if this risk information is [high], set the marking flag to [1].

The risk table 150 may be prepared beforehand by a user inputting risk information from the input unit 202, or risk information may be received and stored in the controller 201a from another computer (host computer, server or the like) connected to the controller 201a via a network.

Furthermore, the risk table 150 may also be stored beforehand in another computer (host computer, server or the like) connected to the controller 201a via a network. In this case, the marking judging section 135 reads the risk information from the risk table 150 stored on another computer over a network.

In addition, the ID and risk information may be accommodated together beforehand in the bar code affixed to the sample container, and the risk table 150 can be prepared from the risk information read by the bar code reader 217.

According to the controller 201a having this structure, only samples with a high risk of viral infection are marked. Accordingly, a user of the blood analyzer can quickly and easily be informed which samples have a high risk of viral infection, and the risk of viral infection can be reduced by exercising special care in the handling of these samples.

A third embodiment of the sample analyzer of the present invention is described below with reference to the drawings. The sample analyzer of the third embodiment is a blood analyzer in which the internal structure of the controller 201 (FIG. 4) of the previously described blood analyzer 100 has been modified. Accordingly, description of structures other than that of the controller 201 are omitted since these other structures are identical to those of the blood analyzer 100.

Figure 12:
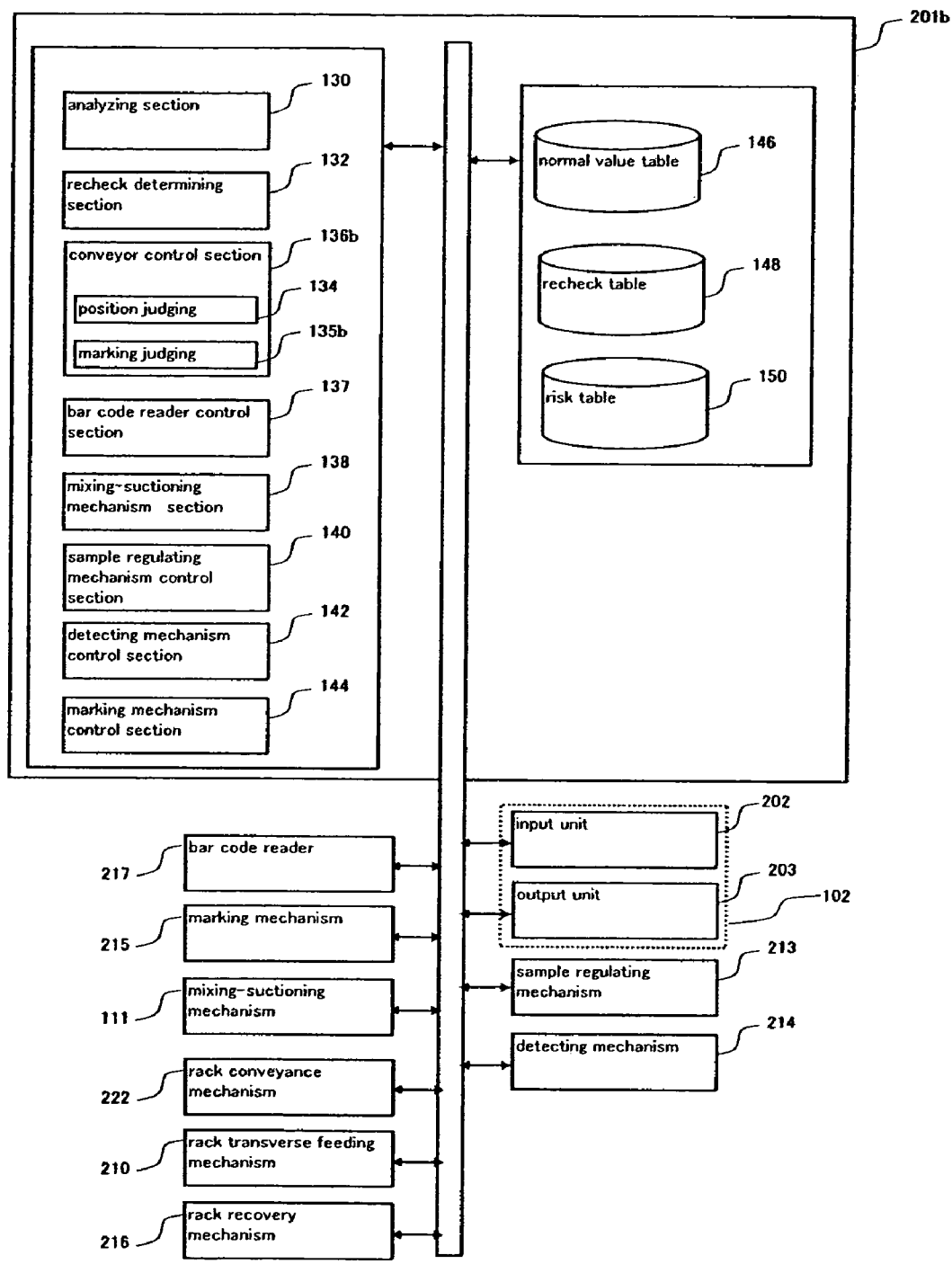
FIG. 12 is an illustration of a controller 201b.

FIG. 12 is an illustration of the controller 201b of the blood analyzer of the third embodiment. The controller 201b is provided with an analyzing section 130, recheck determining section 132, conveyor control section 136b, bar code reader control section 137, mixing-suctioning mechanism control section 138, sample regulating mechanism control section 140, detecting mechanism control section 142, marking mechanism control section 144, normal value table 146, recheck table 148, and risk table 150. The conveyor control section 136b is provided with a position judging section 134, and a marking judging section 135b. The controller 201b is connected to the rack conveyance mechanism 222, rack transverse feeding mechanism 210, rack recovery mechanism 216, mixing-suctioning mechanism 111, input unit 202, output unit 203, sample regulating mechanism 213, detecting mechanism 214, marking mechanism 215, and bar code reader 217.

When a target sample container 200 is set at the marking position M (see FIG. 2), the marking judging section 135b judges whether a recheck is needed using the recheck table 148, and judges the content of the risk information using the risk table 150. Then, if the judgment is that a recheck is [needed], and the target sample risk information is [high], the marking judging section 135b executes a process to set the marking flag at [1].

According to the controller 201b having this structure, only samples which need to be rechecked, and samples with a high risk of viral infection, are marked. Accordingly, a user of the blood analyzer can quickly and easily be informed which samples among samples needing a recheck have a high risk of viral infection, and the risk of viral infection of the user can be reduced by exercising special care in the handling of these samples.

When, for example, a user manually prepares a smear specimen for rechecking, there is a high risk of viral infection because the user must open the cap of the sample container. If the sample analyzer of the third embodiment is used and a smear preparation is necessary, a user can exercise particular care in the handling of the specimen and the risk of viral infection is reduced because the virus infected samples are marked.

Furthermore, the marking judging section 135b may also be constructed such that the marking flag is only set at [1] if a recheck is [needed] and/or the risk information is [high], and otherwise [1] is not input.

Although all of the previously described embodiments are blood analyzers (hematocytometer), the present invention is not limited to these examples and may be adapted to various samples analyzers, such as blood coagulation measuring devices, immunity measuring devices, biochemical analyzers, urine analyzers, industrial particle analyzers ,and the like, and combinations thereof.

Although the above embodiments have been described in terms of a sample analyzer provided with a conveyor, the present invention may be applied to sample analyzers in which a user places sample containers one at a time in a sample suctioning section (for example, the sample analyzer described in United States Patent Publication No. 2002-0034824).

Figure 13:
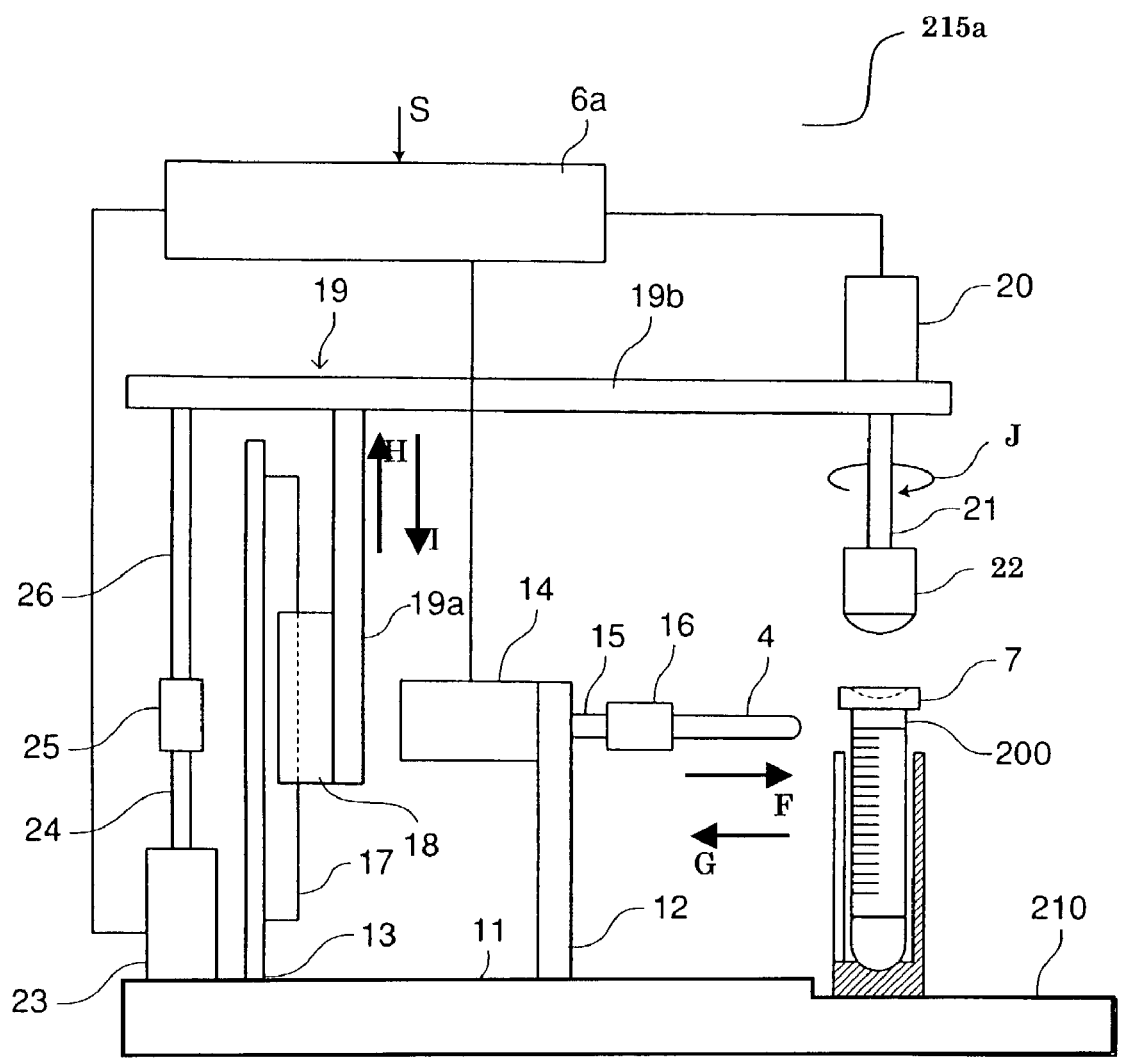

FIG. 13 illustrates the structure of another embodiment of the marking mechanism. As shown in the drawing, the marking mechanism 215a has frames 12 and 13 arranged in a vertical direction on the transverse feeding mechanism 210, and an electric linear actuator 14 mounted on the top end of the frame 12. A marking pen 4 is connected to a drive rod 15 of the linear actuator 14 via a holder 16, so as to move the marking pen 4 in horizontal directions (arrow direction F and arrow direction G) via the drive of the linear actuator 14.

A guide rail 17 is fixedly attached to the frame 13 in a vertical direction, and a slide block 18 is mounted on the guide rail 17 so as to be slidable in vertical directions (arrow direction H and arrow direction I).

A perpendicular part 19a of a T-shape frame 19 is fixedly attached to the slide block 18, and a motor 20 having an output shaft 21 facing downward is arranged on one end of a horizontal part 19b. An elastic member 22 is attached to the tip of the output shaft 21, so as to be rotated in the arrow direction J via the motor 20.

A shaft 26 is attached in a vertical direction to the other end of the horizontal part 19b of the frame 19. The shaft 26 is connected to a drive rod 24 of an electric linear actuator 23 via a coupling 25. The electric linear actuator 23 is fixedly attached to the transverse feeding mechanism 210.

A drive control unit 6a is provided with a drive circuit for driving the motor 20, and the linear actuators 14 and 23, and receives output signals S from the marking mechanism control section 144 (see FIG. 4) and the like so as to drive the motor 20 and the linear actuators 14 and 23 as follows.

First, the elastic member 22 is lowered in a vertical direction by the drive of the linear actuator 23, and stops when the elastic member 22 presses against the cap 7 of the sample container 200 with a predetermined pressure. Then, the marking pen 4 is moved in the arrow direction F via the drive of the linear actuator 14, and stops when the tip of the marking pen 4 contacts the sample container 200.

Next, when the elastic member 22 is rotated 360 degrees via the drive of the motor 20, the sample container 200 is also rotated 360 degrees together with the elastic member 22. In this way, the marking pen 4 applies ink (marks) to the side of the container. Thereafter, the elastic member 22 and the marking pen 4 are returned to their original positions.

If the marking mechanism 215a is used, the sample analyzer of the present invention may be used for sample containers that do no have caps (top part open).

Although the marking mechanism is provided with a single marking pen in the above embodiments, two or more marking pens of different colors (for example, a red marking pen and a blue marking pen) also may be provided.

For example, in the sample analyzer of the first embodiment, the marking judging section 135 (see FIG. 4) may be constructed so as to operate the blue marking pen when the number of erythrocytes is within the normal range and the number of leukocytes is outside the normal range, and operate the red marking pen when the number of erythrocytes and number of leukocytes are both outside the normal range. In this way, a user can judge whether only the leukocytes are abnormal, or both erythrocytes and leukocytes are abnormal by simply looking at the color of the mark affixed to the sample container, thereby promoting rapid checking.

The marking mechanism of the sample analyzer of the third embodiment also may be provided with two or more marking pens of different colors. In this case, the marking judging section 135b (see FIG. 12) is constructed so as to operate the red marking pen when the sample container contains blood [needing] rechecking and having a [high] risk information, and operate the blue marking pen when the sample container contains blood [needing] rechecking and having [low] risk information. In this way, a user can be informed which samples among the samples needing rechecking have a high risk of infection.

The foregoing detailed description and examples have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A sample analyzer comprising:
a marking unit comprising a plurality of markers for marking a container containing a sample, the markers having different colors from each other; and
a controller for controlling the marking unit based on sample information comprising analysis results of a sample corresponding to a plurality of analysis items, such that containers containing samples taht are judged to need rechecking are marked;
wherein the controller controls the marking unit such that colors of marks on the container are different according to which analysis item meets a predetermined condition for rechecking.

2. The sample analyzer of claim 1, further comprising:
a detector for detecting a signal from the sample;
wherein the controller analyzes the signal detected by the detector, and the information is based on a result of analyzing the signal.

3. The sample analyzer of claim 1, further comprising:
a detector for detecting a signal from the sample;
wherein the controller analyzes the signal detected by the detector, and the information is based on a result of analyzing the signal and risk information representing whether the risk of the sample is high or not.

4. The sample analyzer of claim 1, wherein the marking unit comprises a driving mechanism for driving the markers.

5. The sample analyzer of claim 1, further comprising:
a conveyor for conveying the container to a marking position for marking.

6. The sample analyzer of claim 1, wherein the marking unit comprises a first and a second marker for marking the container, a first driving mechanism for driving the first marker, and a second driving mechanism for driving the second marker.

7. The sample analyzer of claim 2,
wherein the controller comprises a memory for storing a range of normal values corresponding to each analysis item; and
the information is based on the analysis result and the range of normal values.

8. The sample analyzer of claim 4, wherein the driving mechanism drives the markers for marking a cap of the container.

9. The sample analyzer of claim 4, wherein the driving mechanism drives the marker for marking a side of the container.

10. The sample analyzer of claim 5, wherein the controller comprises a control section that judges the position of the container on the conveyor.

11. The sample analyzer of claim 7,
wherein the controller compares the analysis result to the range of normal values; and
the information is based on a result of comparing the analysis result and the range of normal values.

12. A sample analyzer comprising:
a detector for detecting a signal from a sample;
a marking unit comprising a plurality of markers for marking a container containing the sample, the markers having different colors from each other; and
a controller for analyzing the signal detected by the detector for a plurality of analysis items, determining whether the sample is to be rechecked or not for each analysis item based on analyzing results of the signal, and for driving the marking unit to mark the container if at least one of the analyzing results is abnormal such that colors of marks on the container are decided according to an analysis item on which the analyzing result is abnormal.

13. The sample analyzer of claim 12, wherein the controller comprises a memory for storing a range of normal values corresponding to each analysis item, and determines whether the sample is to be rechecked or not based on the analysis result and the range of normal values.

14. The sample analyzer of claim 12, further comprising:
a conveyor for conveying the container to a marking position for marking.

15. The sample analyzer of claim 13, wherein the controller compares the analysis result and the range of normal values, and determines whether the sample is to be rechecked or not based on the result of comparing the analysis result and the range of normal values.

16. The sample analyzer of claim 14, wherein the controller judges a position of the container on the conveyor.

17. The sample analyzer of claim 14, wherein the controller stops the conveyor until it is determined whether the sample is to be rechecked or not.

18. A sample analyzing method comprising:
a) providing a container containing a sample;
b) obtaining the sample from the container;
c) detecting a signal from the obtained sample;
d) analyzing the detected signal for a plurality of analysis items;

e) determining whether marking the container is needed or not for each analysis item based on analyzing results of the signal; and f) automatically marking the container if at least one of the analyzing results is abnormal such that colors of marks on the container are decided according to an analysis item on which that analyzing result is abnormal.

19. The sample analyzing method of claim 18, wherein each of the providing, the obtaining, the detecting, the analyzing, the determining, and the marking is performed successively.

20. A sample analyzing system comprising:

a marking unit comprising a plurality of markers for marking a holding member holding a sample to alert a user of the sample analyzing system, the markers having different colors from each other; and a controller for controlling the marking unit to mark holding members containing samples that are judged to need rechecking;

wherein the controller controls the marking unit such that colors of marks on the container are different according to which analysis item meets a predetermined condition for rechecking.

21. The sample analyzing system of claim 20, wherein the holding member comprises a container for containing the sample.

22. A sample analyzer comprising:

a marking unit comprising a plurality of markers for marking a container containing a sample, the markers having different colors from each other;

a detector for detecting a signal from the sample; and a controller for analyzing the signal for a plurality of analysis items, and for controlling whether the marker marks the container or not based on sample information;

wherein the controller comprises a memory for storing a range of normal values corresponding to each analysis item, and the sample information is based on the analyzing results of the signal for each analysis item and the range of normal values for each analysis item: and wherein the controller controls the marking unit such that colors of marks on the container are decided according to an analysis item on which the analyzing result is out of the range of normal value.

23. The sample analyzer of claim 22, wherein the sample information further comprises risk information representing whether risk of the sample is high or not.

* * * * *

UNITED STATES PATENT AND TRADEMARK OFFICE
CERTIFICATE OF CORRECTION

PATENT NO. : 7,487,061 B2  Page 1 of 1
APPLICATION NO. : 10/442288
DATED : February 3, 2009
INVENTOR(S) : Seido Biwa It is certified that error appears in the above-identified patent and that said Letters Patent is hereby corrected as shown below:

Column 11, claim 1, line 49, after "containers containing samples" replace "taht" with --that--.

Signed and Sealed this

Ninth Day of November, 2010

David J. Kappos
*Director of the United States Patent and Trademark Office*